(12) United States Patent
Gueneron

(10) Patent No.: US 9,074,171 B2
(45) Date of Patent: Jul. 7, 2015

(54) MIXING CONTAINER COMPRISING A SHAFT BEARING IN THE UPPER PART

(75) Inventor: Mareva Gueneron, Auriol (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 127 days.

(21) Appl. No.: 13/257,129

(22) PCT Filed: Mar. 16, 2010

(86) PCT No.: PCT/FR2010/050466
§ 371 (c)(1),
(2), (4) Date: Sep. 16, 2011

(87) PCT Pub. No.: WO2010/106282
PCT Pub. Date: Sep. 23, 2010

(65) Prior Publication Data
US 2012/0003733 A1 Jan. 5, 2012

(30) Foreign Application Priority Data

Mar. 18, 2009 (FR) ..................................... 09 51746

(51) Int. Cl.
*C12M 1/06* (2006.01)
*C12M 1/00* (2006.01)
*C12M 3/00* (2006.01)

(52) U.S. Cl.
CPC ............... *C12M 27/02* (2013.01); *C12M 23/26* (2013.01); *C12M 29/06* (2013.01)

(58) Field of Classification Search
CPC ....... C12M 23/26; C12M 29/06; C12M 27/02
USPC ....................................................... 435/289.1
See application file for complete search history.

(56) References Cited

U.S. PATENT DOCUMENTS

| 4,670,397 | A  |   | 6/1987  | Wegner et al. |
|-----------|----|---|---------|---------------|
| 5,470,152 | A  | * | 11/1995 | Rains ............................. 366/273 |
| 7,384,783 | B2 | * | 6/2008  | Kunas et al. ............... 435/289.1 |
| 2005/0272146 | A1 | * | 12/2005 | Hodge et al. ............... 435/289.1 |
| 2006/0270036 | A1 |   | 11/2006 | Goodwin et al. |
| 2008/0139865 | A1 | * | 6/2008  | Galliher et al. ............... 588/249 |

FOREIGN PATENT DOCUMENTS

EP   1 884 561 A1   2/2008
WO   90/11347 A1   10/1990

OTHER PUBLICATIONS

International Search Report, dated Jul. 28, 2010, from corresponding PCT application.

\* cited by examiner

*Primary Examiner* — Nathan Bowers
*Assistant Examiner* — Gautam Prakash
(74) *Attorney, Agent, or Firm* — Young & Thompson

(57) ABSTRACT

A mixing container includes a flexible container, mixing elements and an upper bearing having a rigid flange. The flange is provided with an insertion passage that fluidically communicates with the inside space on one end and with the outside of the container on the other end. The flange is fixed in a rigid and sealing manner to the upper part of the wall of the container around an insertion opening, the insertion passage and the insertion opening communicating fluidically. The flange also supports, on the inside thereof, an upper bearing that is arranged inside, adjacent to the insertion passage, without preventing the fluidic communication between the insertion passage and the insertion opening. The mixing container is used to receive a biopharmaceutical content to be mixed.

36 Claims, 3 Drawing Sheets

MIXING CONTAINER COMPRISING A SHAFT BEARING IN THE UPPER PART

BACKGROUND OF THE INVENTION

1. Field of the Invention

Figure 1:
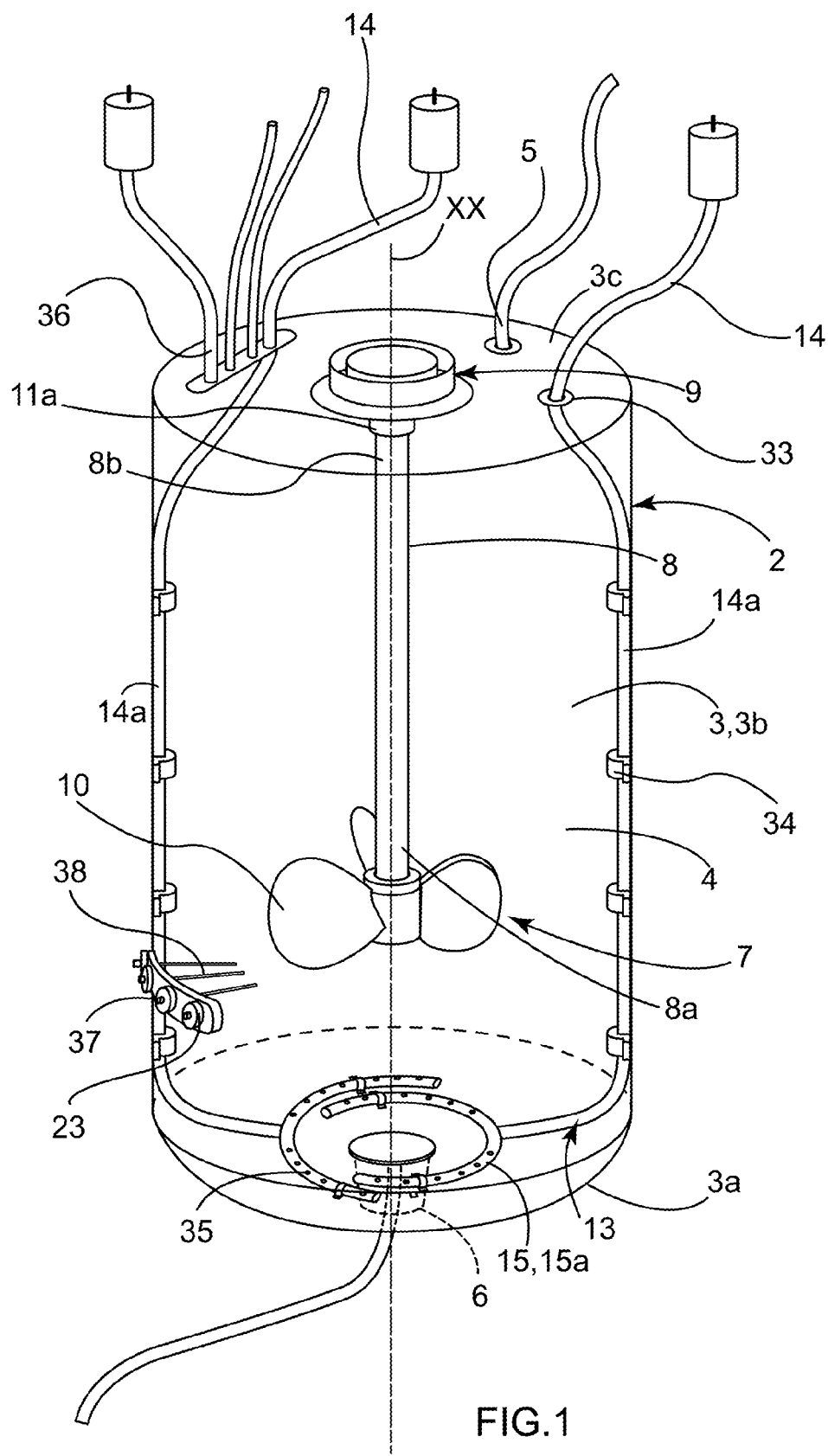

The invention relates to the field of mixing vessels.

Its object more particularly is a mixing vessel that is designed to accommodate biopharmaceutical contents for the purpose of the mixing thereof and such a mixing vessel that acts as a bioreactor.

2. Description of the Related Art

The document US-A-2006/0270036 describes a mixing vessel that comprises an external rigid holding device, a flexible container that is arranged in the housing, means for mixing the contents, and aeration means.

According to one embodiment, the shaft is descending, with the bearing being above, and the aeration means are located perpendicular to the mixing means. According to another embodiment, the shaft, of very small axial size, is upright, with the bearing being below, and the mixing means form a kind of ring placed around the bearing.

Such a mixing vessel has as a drawback that the structure limits the mixing that is achieved and proves particularly unsuitable in the case where it is desired to have a large-capacity container, for example able to reach 5,000 liters.

The document U.S. Pat. No. 4,670,397 relates to a fermenter. The document EP-A-1884561 relates to a ventilated culture receptacle. The document WO 90/11347 relates to a static oxygenator for a culture in suspension.

SUMMARY OF THE INVENTION

The purpose of the invention is to solve the problems posed by the known mixing vessels of the type comprising aeration means and more particularly to optimize the mixing as well as the aeration, including in the case of large-capacity containers that can reach, for example, 5,000 liters.

For this purpose, according to a first aspect, the object of the invention is a mixing vessel that is designed to accommodate biopharmaceutical contents for the purpose of the mixing thereof, comprising:

A flexible container, comprising:
  A wall that has a lower part, a lateral part, and an upper part, delimiting an interior space that can accommodate a certain amount of the contents,
  One or more ports for introducing contents or components of contents into the container, working with one or more introduction openings provided in the container,
  At least one port for draining the contents, working with at least one drain opening,
Means for mixing the contents, comprising:
  At least one shaft, able to be driven in rotation by motor means and to drive in rotation at least one mixing element,
  At least one bearing with which one end part of the shaft works,
  At least one mixing element, able to stir the contents, located in the interior space,
characterized by the fact that it comprises at least one combined introduction/upper bearing port having a rigid flange:
  Provided with an introduction passage in fluid communication with the interior space, on the one hand, and with the exterior of the container, on the other hand,
  Attached in a rigid and airtight way to the upper part of the container wall around an introduction opening, with the introduction passage and the introduction opening being in fluid communication,
  Supporting—from the interior side—an upper bearing that is located in the interior space, adjacent to the introduction passage without preventing the fluid communication between the introduction passage and the introduction opening.

According to one characteristic, the mixing vessel also comprises aeration means that can deliver to the contents a certain amount of aeration gas, comprising aeration gas intake means having at least one tubular element that extends with fluid communication from the exterior of the container to the distribution means and aeration gas distribution means comprising at least one extended distribution element whose wall can allow aeration gas bubbles originating from the intake means to pass, whereby said element is located in the interior space toward the lower part of the container wall.

According to a second aspect, the object of the invention is a mixing vessel that is designed to accommodate biopharmaceutical contents for the purpose of the mixing thereof, comprising:

A flexible container, comprising:
  A wall that has a lower part, a lateral part, and an upper part, delimiting an interior space that can accommodate a certain amount of the contents,
  One or more ports for introducing contents or components of contents into the container, working with one or more introduction openings provided in the container,
  At least one port for draining the contents, working with at least one drain opening,
Means for mixing the contents, comprising:
  At least one shaft, able to be driven in rotation by motor means and to drive in rotation at least one mixing element,
  At least one bearing with which one end part of the shaft works,
  At least one mixing element, able to stir the contents, located in the interior space,
And aeration means that can deliver to the contents a certain amount of aeration gas, comprising:
  Aeration gas intake means having at least one tubular element that extends with fluid communication from the exterior of the container to the distribution means,
  And aeration gas distribution means comprising at least one extended distribution element whose wall can allow aeration gas bubbles originating from the intake means to pass, located in the interior space toward the lower part of the container wall,
characterized by the fact that:
  The at least one shaft is held by the single upper bearing of the combined introduction/upper bearing port and extends over only a part of the distance between the upper part and the lower part of the container wall, whereby the motor means for driving the shaft in rotation is located toward the upper part of the container wall,
  And by the fact that the at least one tubular aeration gas intake element extends into the interior space by being held substantially adjoining or adjacent to the interior surface of the container wall and running through the latter in the upper part by an airtight connection.

According to a first aspect, the object of the invention is a mixing vessel that is designed to accommodate biopharmaceutical contents for the purpose of the mixing thereof, comprising:

A flexible container, comprising:
- A wall that has a lower part, a lateral part, and an upper part, delimiting an interior space that can accommodate a certain amount of the contents,
- One or more ports for introducing contents or components of contents into the container, working with one or more introduction openings provided in the container,
- At least one port for draining the contents, working with at least one drain opening, Means for mixing the contents, comprising:
- At least one shaft, able to be driven in rotation by motor means and to drive in rotation at least one mixing element,
- At least one bearing with which one end part of the shaft works,
- At least one mixing element, able to stir the contents, located in the interior space, And aeration means able to deliver to the contents a certain amount of aeration gas, comprising:
- Aeration gas intake means having at least one tubular element that extends with fluid communication from the exterior of the container to the distribution means,
- And aeration gas distribution means comprising at least one extended distribution element whose wall can allow aeration gas bubbles originating from the intake means to pass, whereby said element is located in the interior space toward the lower part of the container wall, characterized by the fact that:
- The at least one shaft is held by the single upper bearing of the combined introduction/upper bearing port and extends over only a part of the distance between the upper part and the lower part of the container wall, whereby the motor means for driving the shaft in rotation is located toward the upper part of the container wall,
- And by the fact that the at least one extended aeration gas distribution element is spaced radially from the drain port.

According to one embodiment, the at least one shaft is held by the single upper bearing and extends over only a part of the distance between the upper part and the lower part of the wall of the container, with the motor means for driving the shaft in rotation being located toward the upper part of the container wall.

According to one embodiment, the at least one mixing element is spaced substantially far away from the lower part and the upper part of the container wall.

According to one embodiment, the at least one shaft of the mixing means is located in its entirety within the interior space, with the motor means for driving the shaft in rotation operating magnetically, a rotary disk being driven with magnetic poles, where said disk is located on the exterior of the container, operationally works with a rotary disk driven with magnetic poles, and is attached to the at least one shaft in magnetic proximity to the driving rotary disk.

According to one embodiment, the at least one shaft of the mixing means is partly located in the interior space and partly on the exterior of the container, with the motor means for driving the shaft in rotation operating mechanically, a driving rotary shaft, located on the exterior of the container, operationally working with the exterior part of at least one shaft.

According to one embodiment, the mixing means comprise a single descending shaft.

According to one embodiment, the mixing means comprise several descending shafts with substantially parallel axes, each able to drive at least one mixing element in rotation.

According to one embodiment, a shaft of the mixing means supports and drives a single mixing element that is located in a single axial location on the shaft.

According to one embodiment, a shaft of the mixing means supports and drives several mixing elements located at a large number of axial locations on the shaft.

According to one embodiment, a mixing element is spaced substantially far away from the upper part of the container wall at a distance on the order of at least one third of the separation between the lower part and the upper part of the container wall.

According to one embodiment, the at least one tubular aeration gas intake element extends into the interior space by being held substantially adjoining or adjacent to the interior surface of the container wall.

According to one embodiment, the at least one tubular aeration gas intake element is at least partly structurally separate from the container wall and is held to it by gluing, welding, or by means of connected holding pieces.

According to one embodiment, the at least one tubular aeration gas intake element is at least partly structurally an integral part of the container wall.

According to one embodiment, the at least one tubular aeration gas intake element passes through the container wall by an airtight connection.

According to one embodiment, the at least one tubular aeration gas intake element passes through the container wall in the upper part.

According to one embodiment, the at least one extended aeration gas distribution element is held adjoining or adjacent to the interior surface of the lower part of the container wall.

According to one embodiment, the at least one extended aeration gas distribution element is at least partly structurally separate from the container wall and held to it by gluing, welding, or by means of connected holding pieces.

According to one embodiment, the at least one extended aeration gas distribution element is at least partly structurally an integral part of the container wall.

According to one embodiment, the at least one extended aeration gas distribution element does not pass through the wall of the container.

According to one embodiment, the at least one extended aeration gas distribution element comprises a wall that is provided with a large number of dispersed holes that can allow bubbles of aeration gas originating from the intake means to pass.

According to one embodiment, the large number of holes that can allow bubbles of aeration gas originating from the intake means to pass are oriented with different axes of inclination with respect to the vertical line.

According to one embodiment, the holes of the large number of holes are either of the same size or of different sizes.

According to one embodiment, the at least one extended aeration gas distribution element has, in a transverse straight cross-section, a circular or pseudo-circular or elliptical or pseudo-elliptical shape.

According to one embodiment, the at least one extended aeration gas distribution element comprises at least one complete ring that is closed on itself, in circular communication that may or may not be continuous.

According to one embodiment, the at least one extended aeration gas distribution element comprises at least one incomplete ring that is open relative to itself.

According to one embodiment, the incomplete ring has an angular opening of between approximately 180° and 270°.

According to one embodiment, the at least one extended aeration gas distribution element comprises at least one ring and at least one transverse element in fluid communication.

According to one embodiment, the at least one ring of at least one extended aeration gas distribution element is essentially centered on the drain port.

According to one embodiment, the aeration means comprise a single set of aeration gas intake means and aeration gas distribution means.

According to one embodiment, the aeration means comprise several separate sets of intake means of one or more aeration gases and means for distributing aeration gas(es).

According to one embodiment, a set of aeration means comprises a single tubular aeration gas intake element that communicates with a single extended aeration gas distribution element, or a single tubular aeration gas intake element that communicates with several extended aeration gas distribution elements, or several tubular aeration gas intake elements that communicate with a single extended aeration gas distribution element, or several tubular aeration gas intake elements that communicate with several extended aeration gas distribution elements.

According to one embodiment, it comprises several separate extended aeration gas distribution elements, characterized by the fact that at least some of several extended aeration gas distribution elements are located in a large number of radial locations in the interior space toward the lower part of the container.

According to one embodiment, the several separate extended aeration gas distribution elements are radially spaced substantially far away from the drain port to the vicinity of the lateral part of the container wall.

According to one embodiment, an extended aeration gas distribution element is radially spaced substantially far away from the drain port by a distance on the order of at least one-fifth of the diameter of the lower part of the container wall.

According to one embodiment, only the drain projects below the lower part of the container wall.

According to one embodiment, it also comprises one or more gas evacuation ports working with at least one evacuation opening provided in the upper part of the container wall, provided with a nonreturn valve, preventing the introduction of unwanted or undesirable fluids or contaminants into the container.

According to one embodiment, it also comprises one or more ports for introduction, draining, and assembly.

According to one embodiment, the container has a large capacity and can range up to 5,000 liters.

According to one embodiment, it also comprises an external rigid holding device of the container that is filled with its contents, comprising a bottom wall, a peripheral wall, and an upper opening, delimiting a primary housing in which the flexible container, whose interior part rests on the bottom wall and whose lateral part is applied, when the container is filled with its contents, against the peripheral wall, is arranged in a removable manner.

According to one embodiment, the external rigid holding device also comprises a secondary housing below the bottom wall for housing and for protection of the drain and, if necessary, the drive motor means of the mixing means when it is provided in the lower part.

According to one embodiment, the external rigid holding device also comprises heating means, and the flexible container is made of a material that has a certain thermal conductivity such that the implementation of the heating means makes it possible to heat the contents, and, if necessary, means for monitoring the temperature of the container and means for controlling the heating means.

According to one embodiment, the container can be found in three extreme states: a disassembled state of the external rigid holding device in which the container can be arranged flattened on itself; an assembled state of the external rigid holding device in which the container, empty of contents, is arranged in the primary housing of the holding device by resting on the bottom wall; and an assembled state of the external rigid holding device in which the container, filled with its contents, is arranged in the primary housing of the holding device by resting on the bottom wall and by being applied against the peripheral wall.

According to one embodiment, a bioreaction is produced there, with the mixing vessel being a bioreactor.

BRIEF DESCRIPTION OF THE DRAWING FIGURES

Several embodiments of the invention will now be described using drawings in which:

FIG. 1 is a perspective view of a possible embodiment of a mixing vessel whose external rigid holding device is not shown.

Figure 2B:
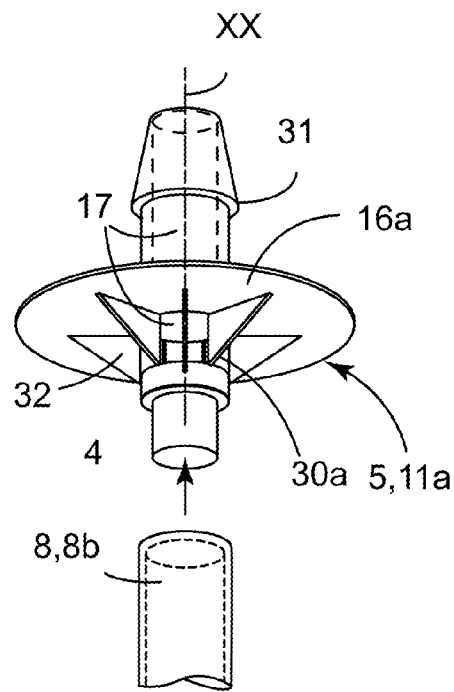
Figure 2C:
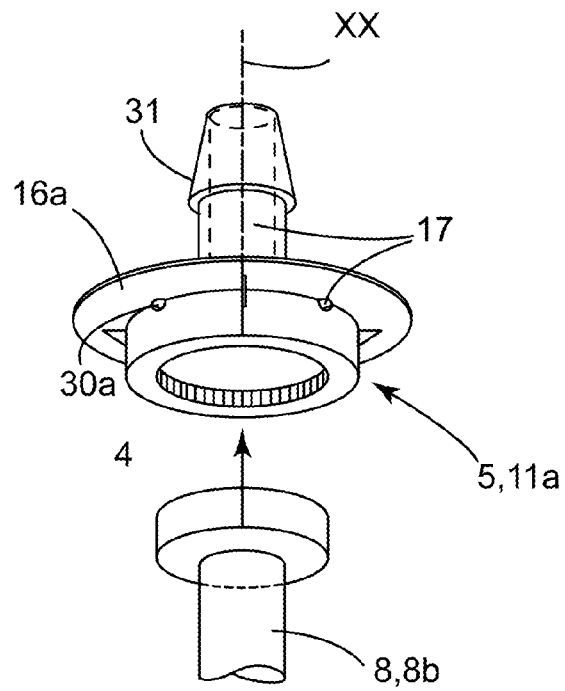
Figure 2A:
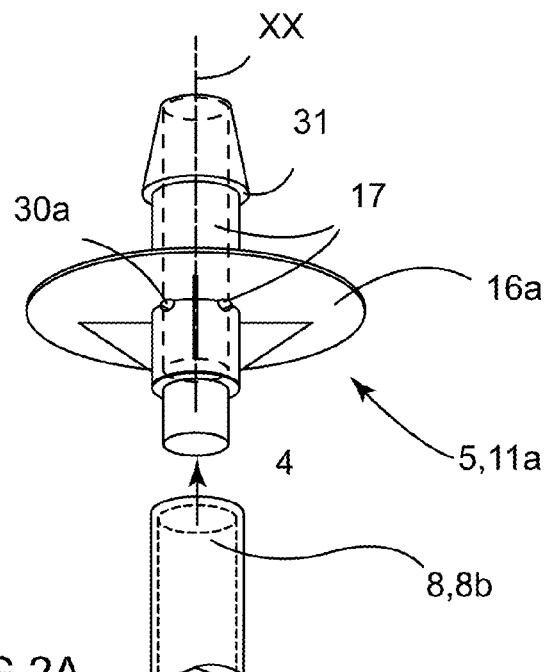

FIGS. 2A, 2B, and 2C are three perspective views of three embodiments of a combined introduction/upper bearing port that is designed to be part of the mixing vessel.

Figure 3:
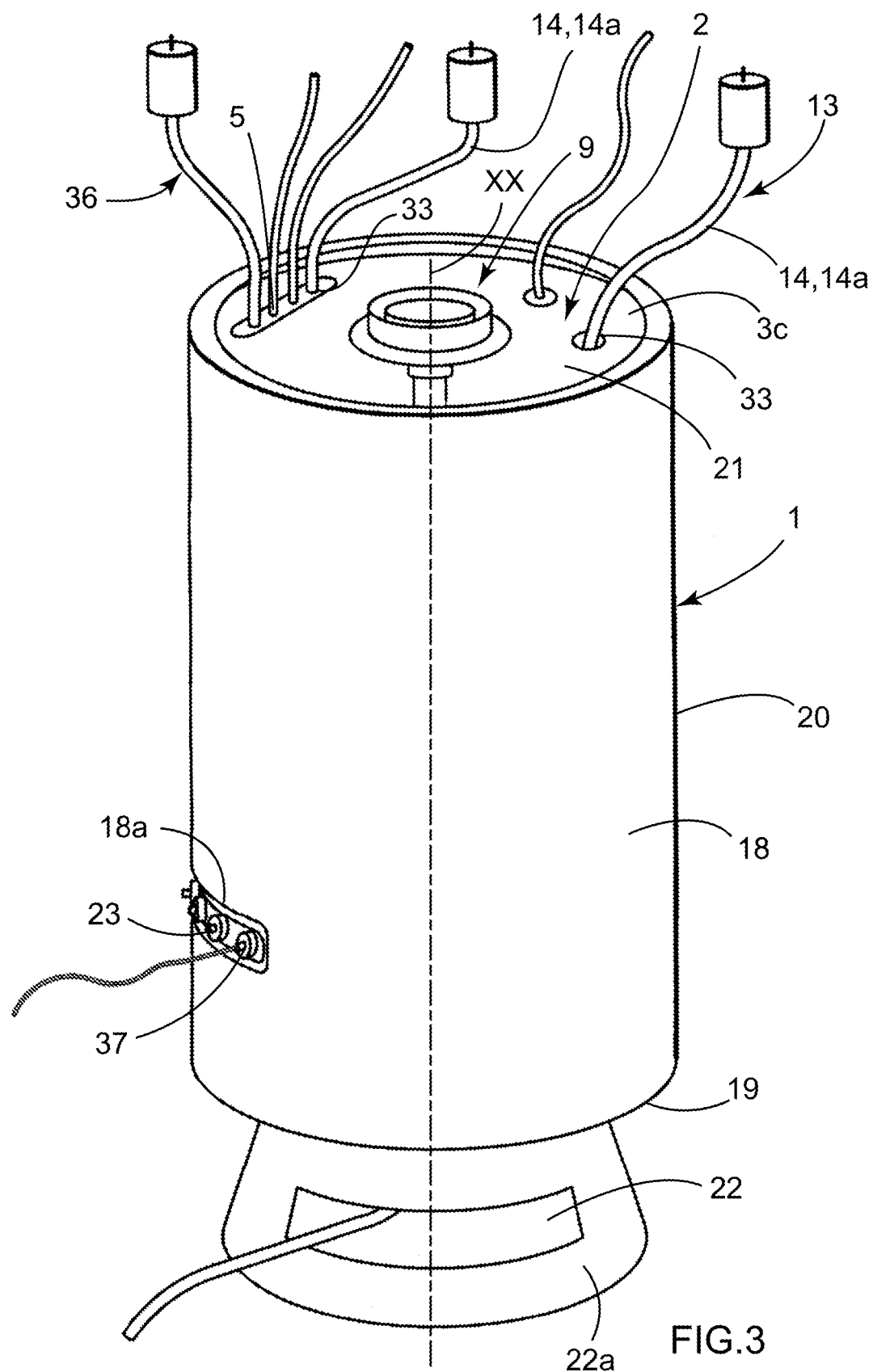

FIG. 3 is an exterior perspective view of the mixing vessel showing the external rigid holding device.

DETAILED DESCRIPTION OF THE INVENTION

A mixing vessel 1 according to the invention is designed to accommodate biopharmaceutical contents C for the purpose of the mixing thereof or, if necessary, for the purpose of a bioreaction, with the mixing vessel 1 then being a bioreactor.

The contents C comprise one or at least one liquid phase. If necessary, the contents C are produced from several components $C_1$, $C_2$, ... of which at least one is in the liquid phase and of which one or more can be in the solid phase, such as powder. If necessary, in the case of a bioreactor, the contents C also comprise cells, micro-organisms, . . . .

The mixing vessel 1 has a primary XX axis that is vertical.

The mixing vessel 1 first comprises a flexible container 2. This flexible container 2 is formed by a wall 3, made of one or more sections that are made integral with one another, having a lower part $3a$, a lateral part $3b$, and an upper part $3c$, delimiting an interior space 4 that can accommodate a certain amount of the contents C.

According to one embodiment, the flexible container 2 is disposable.

The flexible container 2 can have a capacity that ranges up to 5,000 liters based on requirements and applications.

The words "vertical," "horizontal," "upper," and "lower" refer to the situation in which the mixing vessel 1 is in a position that is capable of its operation. It is understood, however, that the mixing vessel 1 can occupy other positions or have other states, for example because it is not in operation. The word "vertical" is not to be understood in a narrow sense, but in the sense meaning from higher to lower and vice versa.

In contrast, the words "interior" and "exterior" refer respectively to what is located inside and outside of the container 2.

Finally, the words "axial," on the one hand, and "radial" and "transverse," on the other hand, refer to that which extends in or parallel to or essentially parallel to the XX axis, on the one hand, and perpendicularly or orthogonally or essentially perpendicularly or orthogonally to the XX axis, on the other hand.

The mixing vessel 1 comprises one or more through ports 5 for introducing the contents C or components $C_1, C_2, \ldots$ of the contents C into the container 2, working with one or more introduction openings provided in the container 2.

The mixing vessel 1 also comprises at least one through port 6 for draining the contents C from the container 2, working with at least one drain opening provided in the container 2. Naturally, the drain port 6 is able to be sealed each time as necessary and in contrast can be open for draining.

In this document, "port" is defined as a connecting means or physical connection. Such a port is a through port when it involves ensuring a linking function between the interior and the exterior of the container 2, for example for the introduction or the drainage of what is to be arranged or is arranged in the container 2. Such a port can also be a non-through port when it involves ensuring a holding function of an element of the mixing vessel.

Pipes, pockets, and tanks, if necessary flexible ones, can be associated with the ports 5, in fluid communication and with an airtight—and, if necessary, removable—connection. Likewise, pipes, pockets, and tanks, if necessary flexible ones, can be associated with ports 6, in fluid communication and with an airtight—and, if necessary, removable—connection. These pipes, pockets, and tanks 5b and 6b are located and extend on the exterior of the mixing vessel 1 and are connected in a suitable manner to intakes and drains, respectively. These pipes, pockets, and tanks are adapted—in particular regarding their size—to the nature of what they contain or ensure the passage. The airtight—and, if necessary, removable—connection is ensured by any suitable device, as it is known in the field of the invention.

In the embodiment shown in FIG. 1, the introduction ports 5 are arranged in the upper position of the mixing vessel 1, and the introduction openings are provided in the upper part 3c of the wall 3, while the drain port 6 is arranged in the lowest position of the mixing vessel 1, and the drain opening is provided in the lower part 3a of the container 2, in its lowest region. If necessary, one (or more) introduction port(s) 5 is/are arranged in the lower position of the mixing vessel 1, and the corresponding introduction opening is provided in the lower part 3a of the container 2 or in the lower region of the lateral part 3b.

The mixing vessel 1 also comprises means 7 for mixing the contents of the container 2. Mixture means that which is located in the interior space 4 of the container 2, whether it is the contents C, or a part of its components, and/or only a part of the total amount that is to be arranged there.

First, the mixing means 7 comprise at least one descending shaft 8, able to be driven in rotation by motor means 9 and to drive in rotation at least one mixing element 10.

Second, the mixing means 7 comprise at least one upper bearing 11a, adjacent to the upper part 3c of the wall 3, with which the upper part 8b of the shaft 8 works.

Third, the mixing means 7 comprise at least one mixing element 10, able to stir the contents, located in the interior space 4.

The mixing vessel 1 also comprises aeration means 13 that can deliver a certain amount of aeration gas to the contents. Aeration means that which is located in the interior space 4 of the container 2, whether it is the contents C or a part of its components, and/or only a part of the total amount that is to be arranged there.

First, the aeration means 13 comprise aeration gas intake means 14 that have at least one tubular element 14a that extends with fluid communication from the exterior of the container 2 to the distribution means 15.

Second, the aeration means 13 comprise the aeration gas distribution means 15 that comprise at least one extended distribution element 15a whose wall can allow the bubbles of aeration gas originating from the intake means 14 to pass. This extended aeration gas distribution element 15a is located within the interior space 4, toward the lower part 3a of the wall 3 of the container 2.

In the embodiment shown in FIGS. 2A, 2B and 2C, the mixing vessel 1 also comprises a combined introduction/upper bearing port 5+11a that has a rigid flange 16a.

"Flange" is defined here as a rigid piece in the general shape of a solid wall, at least essentially flat, arranged flat, and designed for holding.

First, in this case, this flange 16a is provided with a passage 17 for introducing the contents C or components $C_1, C_2, \ldots$ of the contents C, whereby this passage 17 is in fluid communication, on the one hand, with the exterior of the container 2, and, on the other hand, with the interior space 4.

Second, this flange 16a is attached in a rigid and airtight manner to the upper part 3c of the wall 3 of the container 2, around the introduction opening that is provided for this purpose, with the introduction passage and the introduction opening being in fluid communication.

Third, this flange 16a supports, from the interior, the upper bearing 11a, which is located in the interior space 4 by being adjacent to the introduction passage, without preventing the fluid communication between the introduction passage and the introduction opening.

The at least one extended aeration gas distribution element 15a is radially spaced substantially far away from the drain port 6. Extended element 15a means that said element is not incorporated in or in immediate proximity to the drain port 6.

The at least one tubular aeration gas distribution element 14a extends from the extended distribution element 15a, in the interior space 4, along the interior surface of the lower part 3a and the lateral part 3b of the wall 3 of the container 2. The at least one tubular aeration gas distribution element 14a extends to the exterior of the container 2 from—or from the vicinity of—the upper part 3c of the wall 3 of the container 2.

At least one mixing element 10 is spaced substantially far away from the lower part 3a of the wall 3 of the container 2 and from at least one extended aeration gas distribution element 15a. The meaning of this is that the mixing element 10 is not incorporated into or in the immediate vicinity of the wall 3 of the container 2 and of at least one extended aeration gas distribution element 15a.

The preceding structural arrangements are such that the aeration gas bubbles that are distributed from the at least one extended aeration gas distribution element 15a are dispersed into the contents of the interior space 4 by, on the one hand, a first dispersion into the lower region of the interior space 4 that is adjacent to the lower part 3a of the wall 3 of the container 2, by the at least one extended element 15a for dispensing distribution gas, and, on the other hand, a second dispersion by the at least one mixing element 10 in the entire interior space 4 of the container 2.

Because of the flexible nature of the container 2, the mixing vessel 1 also comprises an external rigid—optionally semirigid—holding device 18 of the container 2 that is filled with its contents during the filling, the mixing, and the draining The external rigid holding device 18 comprises a bottom wall 19 and a peripheral wall 20, providing an upper access opening 21 and delimiting a primary housing in which the flexible container 2 is arranged in a removable manner.

The external rigid holding device 18 generally has the geometry, shape and/or dimension that is/are identical to the flexible container 2, so as to reduce the stresses on the welds or the changes in direction in the material of the flexible container 2.

The external rigid holding device 18 comprises the access opening 21 so as to allow the installation and the removal of the flexible container 2.

If necessary, the external rigid holding device 18 comprises other openings for introducing the contents C or the components $C_1$, $C_2$, ... of the contents C and for draining the contents C, or for accessing different elements of the mixing vessel 1 that should be accessible for use.

The lower part 3a of the wall 3 of the container 2 rests on the bottom wall 19, while the lateral part 3b of the wall 3 of the container 2 is applied, when the container 2 is filled with its contents, against the peripheral wall 20.

If necessary, the external rigid holding device 18 also comprises, or forms, a housing or secondary space 22 that is located below the bottom wall 19. This housing or secondary space 22 enables the housing and the protection of the means of the mixing vessel 1 that is located below the container 2. It involves, for example, the pipe, the pocket or the tank that is associated with the drain port. If necessary, the housing or secondary space 22 can be provided in the interior of an underframe 22a, such that the lower part 3a of the wall 3 of the container 2, as well as the bottom wall 19 of the external rigid holding device 18, is separated from the ground or the support surface accommodating the mixing vessel 1, whereby the latter is held in vertical position while allowing access to the drain opening.

If necessary, the external rigid holding device 18 also comprises heating means designed to heat the contents of the container 2. In this case, the flexible container is made of a material that has a certain thermal conductivity such that the implementation of the heating means in question allows the heating of the contents. In this case, and if necessary, means for monitoring the temperature of the contents in the container 2 and means for controlling the heating means are also provided. Such means for monitoring the temperature are carried by one or more ports 23 provided for this purpose.

If necessary, the external rigid holding device 18 also comprises doors, windows, etc. 18a.

According to one embodiment, the bottom wall 19 has the shape of a rounded cap, for example hemispherical or pseudo-hemispherical, whereby the lower part 3a of the wall 3 of the container 2 has the same shape. This structural arrangement, combined with previously disclosed structural arrangements, contributes to the effectiveness of the mixing and the aeration.

The flexible container 2 can be found in three extreme states:

A disassembled state, in which the container 2 is disassembled from the external rigid holding device 18. In this state, the container 2, which is flexible in its entirety, can—when it is empty of contents C—be arranged in a manner that is flattened on itself. This state is most particularly useful for storage or shipping.

An empty assembled state, in which the container 2 is assembled in the external rigid holding device 18, as it was described above, the container 2 being empty of the contents C. In this state, the container 2 is arranged in the primary housing of the holding device 18 by resting on the bottom wall 19.

And finally, a filled assembled state, in which the container is assembled in the external rigid holding device 18, as it was described above, the container 2 being filled with the contents C. In this state, the container 2 is arranged in the primary housing of the holding device 18 by resting on the bottom wall 19 and by being applied against the peripheral wall 20.

For the process of implementing a mixing vessel 1 as it was just described, such a mixing vessel 1 whose drain port 6 is sealed is available, and the contents C or the components $C_1$, $C_2$, ... of the contents C are available.

These contents C or these components $C_1$, $C_2$ ... of the contents C are designed to be accommodated in the container of the mixing vessel 1 and then mixed by means of aeration.

According to the process, first the contents C or the components $C_1$, $C_2$ ... of the contents C are introduced into the container 2 via the port(s) 5.

Then, the mixing means 7 are used to stir the contents of the container 2 located in the interior space 4.

Furthermore, the aeration means 13 are used to deliver a certain amount of aeration gas to the contents of the container 2 located in the interior space 4.

The stirring and the aeration are implemented at least partially simultaneously, and if necessary totally simultaneously.

As a result of the structural arrangements of the mixing vessel 1 and the process that is implemented, the bubbles of the aeration gas are distributed from the at least one extended distribution element 15a, and they are dispersed into the contents C located in the interior space 4 by, on the one hand, a first dispersion into the lower region of the interior space 4 that is adjacent to the lower part 3a of the wall 3 of the container 2, by the at least one extended element 15a for dispensing distribution gas, and, on the other hand, a second dispersion by the at least one mixing element 10 in the entire interior space 4 of the container 2.

The process can be the object of several embodiments. Thus, it is first possible to introduce a component $C_i$ of the contents C, or a part of the components $C_1$, $C_2$ ... of the contents C, into the container 2, and then mixing means 7 and aeration means 13 are implemented in such a way as to deliver a certain amount of aeration gas to the contents, and then the remaining components(s) $C_1$, $C_2$, ... of the contents C is/are introduced into the container 2.

With the mixing vessel 1 comprising, on the one hand, the flexible container 2, and, on the other hand, the external rigid holding device 18, it is possible to proceed as follows.

A start is made from a mixing vessel 1 whose container 2 is disassembled from the external rigid holding device 18 and whose container is empty of contents and arranged in a manner that is more or less flattened on itself.

Then, the container 2 is assembled in the external rigid holding device 18 by arranging it in the primary housing of the latter by resting on its bottom wall 19.

Finally, the contents C or the components $C_1$, $C_2$ ... of the contents C are then introduced into the container 2.

The remainder of the process is as described above.

The mixing vessel can be the object of several embodiments based on different variant embodiments of the mixing means 7, the combined introduction/upper bearing port 5+11a and aeration means 13, whereby the different variants of these means 7 and 13 can, moreover, most often be combined with one another.

More especially, different variant embodiments of the mixing means 7 will now be described.

In the embodiment of the invention, the at least one shaft 8 of mixing means 7 works with a single bearing, namely the upper bearing 11a. The shaft 8 comprises a lower free end 8a that is separated from the lower part 3a of the wall 3 of the container 2, for example located approximately at mid-height of the container 2. The motor means 9 for driving the shaft 8 in rotation is located toward the upper part 3c of the wall 3 of the container 2.

The upper bearing 11a has a rigid flange 16a that is attached rigidly to the upper part 3c of the wall 3 of the container 2. From the interior side, this flange 16a supports the upper bearing 11a that is located in the interior space 4.

According to a possible variant embodiment, the at least one shaft 8 of the mixing means 7 is located in its entirety in the interior space 4. In this case, the motor means 9 for driving the shaft 8 in rotation, toward the upper part 3c of the wall 3 of the container 2, operates magnetically. For this purpose, a driving rotary disk located on the exterior of the container 2, operationally working with a rotary disk being driven with magnetic poles, attached to the at least one shaft 8 with magnetic proximity to the driving rotary disk, is provided.

The upper end 8b of the shaft 8 thus incorporates a magnetic disk that includes a large number of magnets and that is integrated by any means of attachment or design. The magnetic disk is then positioned close to the upper flange 16a. The magnetic disk is connected to the upper flange in such a way as to enable the magnetic motor means to act on the magnets of the magnetic disk, within the width of the upper flange 16a.

For example, the magnetic disk is attached to the shaft 8 by screwing a threaded end of the shaft 8 into a threaded opening in the interior of the magnetic disk. Other means, such as cottered, adhesive, or attached elements, quick attachments, pins, screws, bolts, welding, or the like, as well as the formation of the magnetic disk on the shaft 8 during its manufacturing, can be used to attach the magnetic disk to the shaft 8, without limitation.

To hold the magnetic disk in proper relationship with the upper flange, a hook or a pawl is provided on the magnetic disk, which is engaged on a lip of the upper flange 16a. The particular attachment means of the magnetic disk and the upper flange 16a consisting in the use of the pawl combined with the upper flange 16a and the lip combined with the magnetic disk are not exclusive of others, alternatives such as quick attachments, sections and the like being possible, as soon as the magnetic disk can rotate relatively freely relative to the upper flange 16a.

In addition, to ensure that the magnetic motor means 9 preserves proper alignment with the magnets of the magnetic disk, the upper flange 16a includes a drive coupling that extends upward, starting from the exterior surface of the upper flange 16a.

According to another possible variant embodiment, the at least one shaft 8 of the mixing means 7 is partly located in the interior space 4 and partly on the exterior of the container 2, a sealed rotating connection being provided. In this case, the motor means 9 for driving the shaft 8 in rotation can operate mechanically, with a driving rotary shaft, located on the exterior of the container 2, operationally working with the exterior part of at least one shaft 8.

According to one embodiment, the mixing means 7 comprise a single descending shaft 8. "Descending" is defined as the fact that the shaft 8 generally extends in a top-bottom or vertical direction from the upper bearing 11a.

According to another possible embodiment, the mixing means 7 comprise several shafts 8, with axes that are substantially parallel to one another and all adjoining the upper part 3c of the wall 3 of the container 2. These shafts 8 are each able to drive in rotation at least one mixing element 10. In this embodiment, the mixing vessel 1 comprises several mixing elements 10.

According to a possible embodiment, a shaft 8 of the mixing means 7 supports and drives a single mixing element 10 that is located in a single axial location on the shaft 8. According to another embodiment, a shaft 8 supports and drives several mixing elements 10 located at a large number of axial locations on the shaft 8.

A mixing element 10 can come in the form of a propeller having a hub that supports several blades.

A mixing element 10 is spaced substantially far away from the lower part 3a of the wall 3 of the container 2 and from at least one extended distribution element 15a. According to one embodiment, this spacing or distance is on the order of at least one-quarter of the separation between the lower part 3a and the upper part 3c of the wall 3 of the container 2. In particular, this spacing or distance is on the order of at least one-third of the separation between the lower part 3a and the upper part 3c of the wall 3 of the container 2.

Now, more especially, different variant embodiments of the combined introduction/upper bearing port 5+11a will be described.

The flange 16a that is associated with the upper part 8b of the shaft 8 and that is part of the mixing vessel 1 is more particularly shown in FIGS. 2A, 2B and 2C according to several variant embodiments. In each of these variants, the flange 16a is formed by an essentially rigid material, preferably a rigid plastic material, in the form of a wall or small plate connected to the flexible container 2 in its XX axis, in the center of the upper part 3c. This flange 16a can be connected to the flexible container 2 in any suitable manner so as to form a rigid and hermetic seal between the respective materials, rigid and flexible.

The lower part of the upper flange 16a, which is located in the interior space 4 of the container 2, includes the upper bearing 11a that forms a connecting means that works with the upper part 8b of the shaft 8.

The bearing 11a can be a male bearing in the form of a journal, as shown in FIGS. 2A and 2B, inserted in an open cavity provided in the upper part 8b of the shaft 8. The bearing 11a can be a female bearing in the form of a ring, as shown in FIG. 2C, in the cavity of which is inserted the upper part 8b of the shaft 8.

It is preferred that the shaft 8 adapt to the bearing 11 with minimal friction, such that the shaft 8 can rotate freely on the bearing 11. For this purpose, provisions are made possibly to include a stop bearing between the upper part 8b of the shaft 8 and the bearing 11a, or plain bearings, ball bearings or roller bearings can be provided.

If this is desired, a pawl, which does not significantly compromise the rotation of the shaft 8 on the bearing 11a, can be provided so as to hold the shaft 8 on the bearing 11a.

In one embodiment, an introduction port 5 with an introduction opening provided in the container 2 is associated with the upper flange 16a. The flange 16a is therefore provided with an introduction passage 30 in fluid communication, on the one hand, with the exterior of the container 2 and, on the other hand, with the interior space 4 of the container 2, via the introduction port 5 itself, here in the form of a tube section that comprises an end part that comprises an exterior peripheral projection in the form of a shark's tooth 31, enabling the attachment of the end part of an introduction pipe.

The introduction passage 30 comprises one or more openings 30a that ensure the communication with the interior space 4. These openings 30a are arranged based on the structure of the bearing 11a.

In the variant of FIG. 2A, a large number of radial or essentially radial openings 30a, provided at the—upper-base of the bearing 11a in the form of a journal, dispersed all around, are provided, and these openings 30a empty into the introduction port 5.

In the variant of FIG. 2B, a single, axial opening 30a, provided axially above the—upper-base of the bearing in the form of a journal 11, which—upper-base is lowered relative to the flange 16a by means of brackets 32 arranged radially and axially, is provided, a space thus being provided between this base and the flange 16.

In the variant of FIG. 2C, a large number of radial or essentially radial openings 30a, provided at the—upper-base of the bearing 11a in the form of a ring, dispersed all around, are provided, and these openings 30a empty into the introduction port 5.

Now, different variant embodiments of the aeration means 13 will be described more especially.

The at least one tubular aeration gas intake element 14a extends into the interior space 4 of the container by being held substantially adjoining or adjacent to or against the interior surface of the wall 3 of the container 2 in such a way as to prevent the tubular element 14a from diverging in the container 2, whereas the contents of the latter are stirred by the mixing means 7 at the risk of interfering with the latter.

For this purpose, according to the different variant embodiments that can be considered, the at least one tubular aeration gas intake element 14a is at least partly structurally separate from the wall 3 of the container 2 and held to it by gluing, welding, or by means of holding pieces 34, which are provided and/or at least partly structurally an integral part of the wall 3 of the container 2.

Typical examples of holding pieces 34 are adhesive strips, flanges, tabs or the like that are arranged from place to place along the tubular aeration gas intake element 14a.

The tubular intake element 14a may also be a sleeve. This sleeve is constructed from a length of material that is preferably identical to that from the interior surface of the wall 3 of the flexible container 2, welded or otherwise attached on its longitudinal sides to the interior surface of the wall 3 by being arranged in the interior of the flexible container 2. The tubular region that is encompassed between this sleeve and the interior surface of the wall 3 of the flexible container 2 channels the gas from the exterior of the mixing vessel to the aeration gas distribution means 15.

Upstream (intake of the aeration gas), the at least one tubular aeration gas intake element 14a passes through the wall 3 of the container into the upper part 3c by an airtight connection 33. This structural arrangement makes it possible, on the one hand, to release the region that is located below the lower part 3a that is not encumbered by this tubular element 14a, and, on the other hand, to not be obligated to provide a passage opening for the tubular element 14a in the lower part 3a of the wall 3 of the container 2.

In contrast, the at least one extended element 15a for distribution of aeration gas is held adjoining or adjacent to the interior surface of the lower part 3a of the wall 3 of the container 2.

According to the different variant embodiments that can be considered, the at least one extended aeration gas distribution element 15a is, at least in part, structurally separate from the wall 3 of the container 2 and held to it by gluing, welding or by means of connected holding pieces and/or at least partly structurally an integral part of the wall 3 of the container 2. In any case, the at least one extended aeration gas distribution element 15a does not pass through the wall 3 of the container 2. Such connected holding pieces, when they are provided, can be identical or analogous to those used for the tubular intake element 14a.

Of course, the variant embodiment of the at least one tubular aeration gas intake element 14a complies with that of at least one extended aeration gas distribution element 15a.

The at least one tubular aeration gas intake element 14a extends, from upstream to downstream, from the exterior to the interior of the container 2 and the extended aeration gas distribution element 15a, by the airtight connection 33 in the upper part 3c, then axially along the interior surface of the lateral part 3b up to the interior surface of the lower part 3a, and then radially or essentially radially on the interior surface of the lower part 3a, to the at least one extended aeration gas distribution element 15a that adjoins or is adjacent to the same interior surface of the lower part 3a of the wall 3.

The at least one extended aeration gas distribution element 15a is of the type that comprises a wall that is provided with a large number of holes 35, dispersed on this wall. The tubular aeration gas intake element 14a empties in fluid communication on one side of this wall 15a, whereas the other side of this wall 15a is located in the interior space 4. The holes 35 can allow the passage of the bubbles of aeration gas originating from the intake means 14 to pass toward the interior space 4.

The holes 35 can be the subject of different variant embodiments.

According to a possible variant embodiment, the holes 35 of the large number of holes 35 are oriented with different axes of inclination with respect to the vertical XX axis.

According to other possible variant embodiments, the holes 35 of the large number of holes 35 are either the same size or different sizes.

Thus, the flow rate of the aeration gas exiting from the holes 35 and the discharge orientation of the gas bubbles downstream from the wall of the extended aeration gas distribution element 15a can be adapted based on requirements.

These embodiments apply to a variant embodiment according to which the aeration means 13 comprise a single unit of aeration gas intake means 14 and means 15 for distribution of aeration gas as well as to a variant according to which the aeration means 13 comprise several separate units of intake means 14 of one or more aeration gases and means 15 for distribution of the aeration gas(es).

Such a structural arrangement with several separate units of intake means 14 and means 15 for distribution of one or more aeration gases is particularly well suited to the case where the process requires aeration with several gases, for example aeration with oxygen and aeration with carbon dioxide.

In the case of an arrangement with several separate units of intake means 14 and means 15 for distribution of one or more aeration gases, the different means 15 for distribution of the large number of distribution means 15 have either the same characteristics or have different characteristics that are associated with the type or the volume of gas introduced into the contents C. These different characteristics can include, but in a nonlimiting way, the size and the number of holes 35. According to a variant embodiment, the aeration means 13 are such that a single extended distribution element 15a is associated with a single tubular intake element 14a. According to other variant embodiments, several extended distribution elements 15a are associated with a single tubular intake element 14a, or conversely, a single extended distribution element 15a is associated with several tubular intake elements 14a.

The at least one extended aeration gas distribution element 15a can be the object of different variant embodiments.

In one variant embodiment, the at least one extended aeration gas distribution element 15a has, in elevation, a general annular or pseudo-annular shape, which has, in a transverse straight cross-section, a general shape that can be circular or pseudo-circular, or elliptical or pseudo-elliptical. At least one such annular element 15a is in fluid communication with the tubular intake element 14a. According to one variant, at least one, in particular radial, transverse element is associated with the annular element 15a, which makes possible a more dispersed distribution of gas.

As appropriate, the annular element 15a is in the shape of a complete ring that is closed on itself, in circular fluid communication that may or may not be continuous, or is in the shape of an incomplete ring that is open relative to itself. In one embodiment, the angular opening of such an open ring is between approximately 180° and 270°.

In one variant embodiment, such an annular element 15a is essentially centered on the drain port 6.

In one variant embodiment, the aeration means 13 comprise a single unit of aeration gas intake means 14 and means 15 for distribution of aeration gas. In another variant embodiment, the aeration means 13 comprise several separate units of intake means 14 of one or more aeration gases and means 15 for distribution of aeration gas(es).

Such a unit 14+15 of aeration means 13 can be the object of different variant embodiments in that said unit comprises either a single tubular aeration gas intake element 14a that communicates with a single annular element 15a for distribution of aeration gas, or a single tubular element 14a that communicates with several annular elements 15a, or several tubular elements 14a that communicate with a single annular element 15a, or else several tubular elements 14a that communicate with several annular extended elements 15a.

In contrast, in the case where such a unit 14+15 comprises several annular elements 15a for distribution of separate aeration gases, it is possible, in a variant embodiment, that these—or some of these—annular elements 15a are located in several radial locations in the interior space 4 and toward the lower part 3a of the wall 3 of the container 2. In this case, such radial locations can, in a variant embodiment, be radially spaced substantially far away from one another relative to the XX axis between the drain port 6 to the vicinity of the lateral part 3b of the wall 3 of the container 2.

With such an arrangement, the aeration is particularly well dispersed upon its distribution.

As has been stated above, an annular aeration gas distribution element 15a is radially spaced substantially far away from the drain port 6. According to one embodiment, this spacing or distance is on the order of at least one-fifth of the diameter of the lower part of the wall 3 of the container 2.

At least one aeration gas evacuation port 36 that works with at least one evacuation opening provided in the upper part 3c of the wall 3 of the container 2 can be associated operationally with the aeration means 13 that were just described. Such an aeration gas evacuation port 36 can be provided with a non-return valve, preventing the introduction into the container 2 of fluids or contaminants that are unwanted or undesirable. Such an aeration gas evacuation port 36 makes it possible to evacuate the gas that has not been mixed into the contents of the container 2 from the container 2 toward the exterior. Such an aeration gas evacuation port 36 can be in fluid communication with the aeration gas intake for the purpose of recycling.

The mixing vessel 1 can, in certain embodiments, also comprise one or more assembly ports 37, for example of an operational means, able to ensure the holding of an operational element 38 such as typically the collection or the measurement of data and sampling for purposes of analysis.

The invention claimed is:

1. A bioreactor, comprising:
   a flexible container, comprising:
      a wall that has a lower part, a lateral part, and an upper part, delimiting an interior space,
      at least one port configured for introducing contents or components into the container, working with at least one introduction openings provided in the container, and
      at least one port for draining the contents, working with at least one drain opening;
   a mixer, comprising:
      at least one shaft,
      a motor driving the at least one shaft and driving in rotation at least one mixing element,
      at least one bearing with which one end part of the shaft works, and
      at least one mixing element, able to stir the contents, located in the interior space; and
   at least one combined introduction and bearing port having a rigid flange,
      an introduction passage of the flange being in fluid communication with the interior space and with an exterior of the container,
      the flange being attached in a rigid and airtight way to the upper part of the container wall around the one or more introduction openings, with the introduction passage and the one or more introduction openings being in fluid communication, and
      the flange supporting from an interior side an upper bearing that is located in the interior space and is configured to permit fluid communication between the introduction passage and the one or more introduction openings.

2. The bioreactor according to claim 1, further comprising:
   an aerator configured to deliver to the contents aeration gas, comprising an aeration gas intake having at least one tubular element that extends with fluid communication from the exterior of the container to an aeration gas distributor comprising at least one extended distribution element whose wall is configured to allow aeration gas bubbles originating from the intake to pass, whereby said element is located in the interior space toward the lower part of the container wall.

3. The bioreactor according to claim 2, wherein the at least one tubular aeration gas intake element extends into the interior space by being held adjoining or adjacent to the interior surface of the container wall.

4. The bioreactor according to claim 2, wherein the at least one tubular aeration gas intake element is structurally separate from the container wall and held to it by gluing, welding, or by connected holding pieces.

5. The bioreactor according to claim 2, wherein the at least one tubular aeration gas intake element is structurally an integral part of the container wall.

6. The bioreactor according to claim 2, wherein the at least one tubular aeration gas intake element passes through the container wall by an airtight connection.

7. The bioreactor according to claim 2, wherein the at least one extended aeration gas distribution element is held adjoining to the interior surface of the lower part of the container wall.

8. The bioreactor according to claim 2, wherein the at least one extended aeration gas distribution element is either structurally separate from the container wall and held to it by gluing, welding, or by connected holding pieces, or structurally an integral part of the container wall.

9. The bioreactor according to claim 2, wherein the at least one extended aeration gas distribution element does not pass through the wall of the container.

10. The bioreactor according to claim 2, wherein the at least one extended aeration gas distribution element comprises a wall that is provided with dispersed holes that can allow aeration gas bubbles originating from the intake to pass, and, the holes can allow aeration gas bubbles originating from the intake to pass, is oriented with different axes of inclination with respect to a vertical line, with the holes being either the same size or different sizes.

11. The bioreactor according to claim 2, wherein the at least one extended aeration gas distribution element has, in a transverse straight cross-section, a circular or pseudo-circular, or elliptical or pseudo-elliptical shape.

12. The bioreactor according to claim 2, wherein the at least one extended aeration gas distribution element comprises either at least one complete ring that is closed on itself, in circular communication, or at least one incomplete ring that is opened relative to itself, with an angular opening of between approximately 180° and 270°.

13. The bioreactor according to claim 12, wherein the at least one ring of the at least one extended aeration gas distribution element is centered on the drain port.

14. The bioreactor according to claim 2, wherein the at least one extended aeration gas distribution element comprises at least one ring and at least one transverse element in fluid communication.

15. The bioreactor according to claim 2, wherein the aerator comprises either a single set of aeration gas intakes and aeration gas distributor or two or more separate sets of intakes of one or more aeration gases and an aeration gas(es) distributor.

16. The bioreactor according to claim 15, wherein a set of aerators comprises a single tubular aeration gas intake element that communicates with a single extended aeration gas distribution element, or a single tubular aeration gas intake element that communicates with several extended aeration gas distribution elements, or several tubular aeration gas intake elements that communicate with a single extended aeration gas distribution element, or several tubular aeration gas intake elements that communicate with several extended aeration gas distribution elements.

17. The bioreactor according to claim 2, wherein when there are two or more separate extended aeration gas distribution elements, at least some of the extended aeration gas distribution elements being located in a large number of radial locations in the interior space toward the lower part of the container.

18. The bioreactor according to claim 17, wherein the two or more separate extended aeration gas distribution elements are radially spaced from the drain port to a vicinity of the lateral part of the container wall.

19. The bioreactor according to claim 2, wherein an extended aeration gas distribution element is radially spaced from the drain port by a distance on an order of at least one-fifth of a diameter of the lower part of the container wall.

20. The bioreactor according to claim 2, further comprising one or more gas evacuation ports that work with at least one evacuation opening provided in the upper part of the container wall, provided with a nonreturn valve, preventing the introduction of unwanted or undesirable fluids or contaminants into the container.

21. The bioreactor according to claim 1, wherein the at least one shaft is held by the single upper bearing and extends over only a part of the distance between the upper part and the lower part of the container wall, whereby the motor is located toward the upper part of the container wall.

22. The bioreactor according to claim 1, wherein the at least one mixing element is spaced from the lower part and the upper part of the container wall.

23. The bioreactor according to claim 1, wherein the at least one shaft of the mixer is either located entirely in the interior space, with the motor operating magnetically, a rotary disk being driven with magnetic poles, where said disk is located on the exterior of the container, operationally works with a rotary disk driven with magnetic poles, and is attached to the at least one shaft in magnetic proximity to the driving rotary disk, or is partly located in the interior space and partly on the exterior of the container, with the motor operating mechanically, a driving rotary shaft, located on the exterior of the container, operationally working with the exterior part of at least one shaft.

24. The bioreactor according to claim 1, wherein the mixer comprises either a single descending shaft or several shafts descending from parallel axes, each able to drive in rotation at least one mixing element.

25. The bioreactor according to claim 1, wherein a shaft of the mixer supports and drives either a single mixing element that is located in a single axial location on the shaft or several mixing elements that are located at a large number of axial locations on the shaft.

26. The bioreactor according to claim 1, wherein a mixing element is spaced from the upper part of the container wall, at a distance on the order of at least one third of a separation between the lower part and the upper part of the container wall.

27. The bioreactor according to claim 1, wherein only the drain projects under the lower part of the container wall.

28. The bioreactor according to claim 1, further comprising one or more ports for introduction, draining, and assembly.

29. The bioreactor according to claim 1, wherein the container has a capacity up to 5,000 liters.

30. The bioreactor according to claim 1, further comprising an external rigid holding device of the container that is filled with its contents, comprising a bottom wall, a peripheral wall, and an upper opening, delimiting a primary housing in which the flexible container, whose interior part rests on the bottom wall and whose lateral part is applied, when the container is filled, against the peripheral wall, is arranged in a removable manner.

31. The bioreactor according to claim 30, wherein the external rigid holding device also comprises:
   a secondary housing below the bottom wall for housing and for protection of the drain and a drive motor of the mixer when provided in the lower part and a heater, and
   the flexible container is made of a material that has a thermal conductivity that makes it possible to heat the contents, and, a temperature monitor of the container and a controller of the heater.

32. The bioreactor according to claim 30, wherein the container can be found in three states:
   a disassembled state of the external rigid holding device in which the container can be arranged flattened on itself;
   an assembled state of the external rigid holding device in which the container, empty of contents, is arranged in the primary housing of the holding device by resting on the bottom wall; and
   an assembled state of the external rigid holding device in which the container, filled with its contents, is arranged in the primary housing of the holding device by resting on the bottom wall and by being applied against the peripheral wall.

33. The bioreactor according to claim 1, wherein a bioreaction is produced inside the bioreactor.

34. The bioreactor according to claim 1, wherein
the introduction passage is in a form of a tube section the comprises and end part having an exterior peripheral projection shaped like a shark's tooth, or
the flange is provided with a plurality of radial openings provided at an upper base of the upper bearing in a form of a journal, and the radial openings empty into the introduction port, or
the bearing is rotatable.

35. A bioreactor, comprising:
a flexible container, comprising:
  a wall that has a lower part, a lateral part, and an upper part, delimiting an interior space that can accommodate contents,
  one or more ports configured for introducing contents or components of contents into the container, working with one or more introduction openings provided in the container, and
  at least one port configured for draining the contents, working with at least one drain opening;
a mixer, comprising:
  a motor driving least one shaft and configured to drive in rotation at least one mixing element,
  at least one bearing with which one end part of the shaft works, and
  at least one mixing element, able to stir the contents, located in the interior space; and
an aerator configured to deliver to the contents aeration gas, comprising:
  an aeration gas intake having at least one tubular element that extends with fluid communication from an exterior of the container to an aeration gas distributor, and
  the aeration gas distributor comprising at least one extended distribution element with a wall that can allow aeration gas bubbles originating from the intake to pass, located in the interior space toward the lower part of the container wall,
wherein:
the at least one shaft is held by the single upper bearing of a combined introduction and bearing port and extends over only a part of the distance between the upper part and the lower part of the container wall, whereby the motor driving the shaft in rotation is located toward the upper part of the container wall, and the at least one tubular aeration gas intake element extends into the interior space by being held adjacent to the interior surface of the container wall and running through the container wall in the upper part by an airtight connection.

36. A bioreator, comprising:
a flexible container, comprising:
  a wall that has a lower part, a lateral part, and an upper part, delimiting an interior space that can accommodate contents,
  at least one for introducing contents or components of contents into the container, working with one or more introduction openings provided in the container, and
  at least one port for draining the contents, working with at least one drain opening;
a mixer, comprising:
  a motor driving least one shaft and to drive in rotation at least one mixing element,
  at least one bearing with which one end part of the shaft works,
  at least one mixing element, able to stir the contents, located in the interior space; and
an aerator that can deliver to the contents aeration gas, comprising:
  an aeration gas intake having at least one tubular element that extends with fluid communication from an exterior of the container to a distributor, and
  the distributor comprising at least one extended distribution element whose wall can allow aeration gas bubbles originating from the intake to pass, located in the interior space toward the lower part of the container wall, wherein:
the at least one shaft is held by the single upper bearing of a combined introduction and bearing port and extends over part of a distance between the upper part and the lower part of the container wall, whereby the motor is located toward the upper part of the container wall, and
the at least one extended aeration gas distribution element is radially spaced from the drain port.

* * * * *